US00PP08304P

United States Patent [19]

Schumann

[11] Patent Number: Plant 8,304

[45] Date of Patent: Jul. 13, 1993

[54] GERANIUM PLANT NAMED FISOPA

[75] Inventor: Ingeborg Schumann, Münster, Fed. Rep. of Germany

[73] Assignee: Florfis AG, Binningen, Switzerland

[21] Appl. No.: 779,294

[22] Filed: Oct. 18, 1991

[51] Int. Cl.[5] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisopa, particularly characterized by the combined features of large light pink flowers, double flower form, early flower response, semi-spherical shaped umbels, prolific flower production, medium green leaves without zonation, medium growth habit, and good rooting ability.

1 Drawing Sheet

The present invention comprises a new and distinct cultivar of geranium, botanically known as *Pelargonium peltatum L'Hert*, and hereinafter referred to by the cultivar name Fisopa.

Fisopa is a product of planned breeding program which had the objective of creating new geranium cultivars with rose/pink flower color, double flower form, early flower response and rich flower production.

Fisopa was originated from a hybridization made by the inventor Ingeborg Schumann in a controlled breeding program in Galdar, Gran Canaria, Spain in 1986. The female parent was identified by the number K 85/238/3 and resulted from crossing a hybrid geranium cultivar resulting from a cross between Salmon Queen and Amethyst, with a hybrid geranium resulting from a cross between Salmon Queen and Yale. The male parent of Fisopa was identified by the number K 85/254/3 and was derived from crossing a hybrid cultivar resulting from a cross between Italian Gem and El Gaucho, with an unnamed seedling characterized by its single red flowers.

Fisopa was discovered and selected as one flowering plant within the progeny of the stated cross by Ingeborg Schumann in 1987 in a controlled environment in Galdar, Gran Canaria, Spain.

The first act of asexual reproduction of Fisopa was accomplished when vegetative cuttings were taken from the initial selection in February 1988 in a controlled environment in Hillscheid, Federal Republic of Germany by, or under the supervision of, Ingeborg Schumann.

Horticultural examination of rooted cuttings initiated in May 1988 and continuing thereafter has demonstrated that the combination of characteristics as herein disclosed for Fisopa are firmly fixed and are retained through successive generations of asexual reproduction.

Fisopa has not been observed under all possible environmental conditions. The phenotype may vary somewhat with variations in environment such as temperature, light intensity and day length, without, however, any variance in the genotype. The following observations measurements, and comparisions describe plants grown in Hillscheid, Federal Republic of Germany under greenhouse conditions which approximate those generally used in commercial practice.

The following traits have been repeatedly observed and are determined to be basic characteristics of Fisopa, which in combination distinguish this geranium as a new and distinct cultivar:

1. Large double flowers
2. Light pink flower color, with dark red markings on petals
3. Early flower response in spring and rich flowering throughout the year
4. Uniform, semi-spherical shaped umbels
5. Medium green leaves without zonation
6. Medium growth habit
7. Good rooting ability of cuttings Of the many commercial cultivars known to the present inventor, the most similar in comparison to Fisopa is the cultivar Galilee, originated in France. Reference is made to attached Chart A which compares certain characteristics of Fisopa to those same characteristics of Galilee. In general comparison to Galilee, Fisopa has very similar flowers and umbels, but is different in plant habit. Flower response is earlier than with Galilee. A further difference is that the plant branches very easily which results in much greater inflorescence, with almost twice the number of flowers during the year. The pink flower color of both cultivars is very similar, although Galilee appears to have a slightly deeper shade of pink when its flowers are just opening.

The accompanying color photographic drawing comprises a side elevational view showing typical flower and foliage characteristics of Fisopa, with colors being as true as possible with illustrations of this type.

In the following description color references are made to The Royal Horticultural Society Color Chart. The color values were determined indoors from flowers taken from plants grown outdoors in June at Hillscheid, Federal Republic of Germany.

Classification:

*Botanical.*—A hybrid of the species *Pelargonium peltatum L'Hert.*

*Commercial.*—Ivy geranium, cv. Fisopa.

INFLORESCENCE

A. Umbel:

*Average diameter.*—82 mm.

*Average depth.*—50 mm.

*Peduncle length.*—120 mm.

*Pedicel length.*—21 mm.

*Number of flowers per umbel.*—8.

B. Corolla:

*Average diameter.*—50 mm.

*Form.*—double.

*Number of Petals.*—16–17.

*Color (general tonality from a distance of three meters).*—pink.

*Color of top surface after flower has fully opened.*—R.H.S. between 73B and 67D.

*Markings on petals.*—dark red marks on upper petals consisting of two veins and a small dot in the middle of the petal; lower petals sometimes show weak markings of same kind, as will inner petals near upper petals.

*Color of lower surface.*—Light pink, almost white, with purple veins.

*Color of sepals.*—Light green.

*Number of sepals.*—6–9.

*Petaloids.*—There is average of two or three small petals with a stamen on top; petaloids are essentially transformed anthers.

C. Bud:

*Shape.*—Elongated.

*Color (sepals).*—Green.

*Color (tips of petals).*—Salmon pink.

D. Reproductive organs:

*Androecium.*—4–6 anthers, only 3–4 fertile, with orange pollen.

*Gynoecium.*—5–6 lobed stigma, red.

E. Spring flowering response period: In Hillscheid, Federal Republic of Germany, in 1989 75% of plants with at least 1 flower opened 11 weeks after planting of unrooted cuttings.

F. Outdoor flower production: The flower count in 1989 in Hillscheid, Federal Republic of Germany, indicated between 180 and 200 umbels per plant for May through September observation period.

G. Durability: Rain resistance is fair. Shatter resistance is good.

H. Seed production: Fisrina is fertile and produces seed after pollination, but sets only a few seeds spontaneously.

PLANT

A. Foliage:

*Form.*—Ivy shaped, with rounded lobes.

*Margin.*—Entire.

*Color (upper surface).*—Medium green, 137B.

*Color (zonation).*—No zonation.

*Tolerance of botrytis.*—Good.

B. General appearance and form:

*Internode length.*—2–3 cm.

*Branching pattern.*—7.8 after 12 weeks of growing time self-pinching.

*Height.*—50 cm in August.

CHART A

| | FISOPA | GALILEE |
|---|---|---|
| Diameter of umbel | 8.3 cm | 8.7 cm |
| Number of umbels per plant | 190 | 99 |
| Growth | medium | medium |
| Plant habit | bushy | loose |
| Branching habit (number of branches per plant | 7.8 | 4.6 |
| Beginning of flowering (percent of flowering plants in 11th week | 75% | 50% |

I claim:

1. A new and distinct cultivar of geranium plant named Fisopa, as illustrated and described.

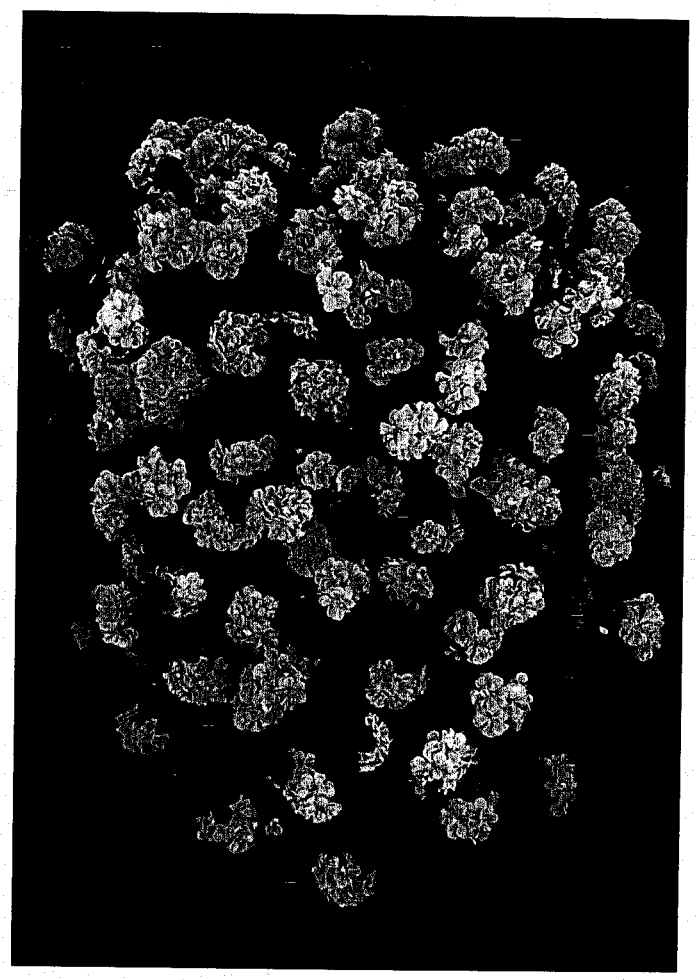

* * * * *